United States Patent [19]

Mittelmeier et al.

[11] Patent Number: 5,397,359
[45] Date of Patent: Mar. 14, 1995

[54] METAL WIRE STRUCTURE FOR ENDOPROSTHETICS

[75] Inventors: Heinz Mittelmeier, Homburg-Schwarzenbach, Germany; Beat Leu, Hergiswil, Switzerland

[73] Assignee: Oscobal AG, Selzach, Switzerland

[21] Appl. No.: 925,739

[22] Filed: Aug. 7, 1992

[30] Foreign Application Priority Data

Aug. 7, 1991 [EP] European Pat. Off. ........... 91810618

[51] Int. Cl.⁶ .................. A61F 2/28; A61F 2/06; A61F 2/30; A61F 2/32
[52] U.S. Cl. ........................................ 623/16; 623/22; 623/18; 623/23; 623/1; 623/11; 623/20
[58] Field of Search ............... 623/18, 16, 23, 22, 623/20, 1, 11

[56] References Cited

U.S. PATENT DOCUMENTS

| | | |
|---|---|---|
| 4,038,703 | 8/1977 | Bokros . |
| 4,064,567 | 12/1977 | Burstein et al. . |
| 4,570,271 | 2/1986 | Sump ..................................... 623/18 |
| 4,654,464 | 3/1987 | Mittelmeier et al. . |
| 4,955,911 | 9/1990 | Frey et al. . |
| 4,969,907 | 11/1990 | Koch et al. . |
| 4,976,738 | 12/1990 | Frey et al. . |
| 4,997,445 | 3/1991 | Hodorek . |
| 5,032,129 | 7/1991 | Kurze et al. . |

FOREIGN PATENT DOCUMENTS

| | | |
|---|---|---|
| 0224890 | 6/1987 | European Pat. Off. . |
| 0278205 | 8/1988 | European Pat. Off. . |
| 0338976 | 3/1989 | European Pat. Off. . |
| 2115576 | 7/1972 | France . |
| 2331320 | 6/1977 | France . |
| 368309 | 5/1963 | Switzerland . |
| 2184458 | 6/1987 | United Kingdom . |
| WO9008520 | 8/1990 | WIPO . |

*Primary Examiner*—David Isabella
*Assistant Examiner*—Debra S. Brittingham
*Attorney, Agent, or Firm*—Marks & Murase

[57] ABSTRACT

The metal wire structure for endoprosthetics is formed of a sintered hollow mesh knitting of elastic metal wires (D), said knitting being preferably manufactured in the manner of a "rete milanese". Said metal wire structure is either used as a coating (1) of an endoprosthesis (3) or, after having been sintered together, as a bone replacement piece.

Such a metal wire structure allows to obtain a good anchorage in the bone, since the pore size of said meshes may be adapted to the local conditions, on one hand, and on the other hand, the remaining elasticity of said meshes allows a suitable transition from said prosthesis to the bone.

18 Claims, 4 Drawing Sheets

METAL WIRE STRUCTURE FOR ENDOPROSTHETICS

The present invention refers to a metal wire structure for endoprosthetics as well as to a method for the manufacture of said wire structure and to an application of the same as a surface of an endoprosthesis or as a bone replacement material. Endoprosthetics of the skeleton has mainly been related to the replacement of destroyed joints, but it is increasingly being used for the replacement of other skeleton sections such as the shafts of members, bones, of the pelvis, as well as for the replacement of vertebral bodies, skull bones and for tooth or denture anchorage. The anchorage of said prostheses in the bone has turned out to be one of the major problems.

Lately, when it has been found that the anchorage of prostheses by means of bone cement leads to considerable problems, the main efforts were directed to provide the prostheses with surfaces with which the bone tissue can durably grow together. In this context, there are different influential factors, such as e.g. the porosity, the material structure, and the bond with the prosthesis. One direction of the development is the use of metal wire meshes, a representative of a series of patents and patent applications being U.S. Pat. No. 4,976,738, which describes a metallic coating of several layers of interweaved metal wire grids, preferably of titanium wires, whose mesh size is inwardly decreasing towards the prosthesis. Although such a coating is being described for the case of plastics prostheses, it is also applicable for metal prostheses. While the problem of the suitable pore size is attempted to be solved here, the elasticity remains insufficient. After sintering it onto a prosthesis surface, said grid will become relatively stiff, and its metal structures are not sufficiently capable of following the elastic movements of the ingrowing and adjoining bone. Therefore, layering such structures onto metal prostheses results in problems because they do not allow a structural transition of elasticity between the relatively stiff metal and the bone tissue or even the spongiosa, so that partly only connective tissue bonds instead of bony bonds are established due to shearing movements in the outer zone.

By using a metal implant coating formed of thin, corrugated sheets it has been attempted to solve the elasticity problem, but other problems result in this case, particularly with respect to the pore size, as well as a relatively expensive manufacture. This bone implant coating is described in U.S. Pat. No. 4,969,907.

Finally, bone replacement materials are known which have been fabricated in the most diverse ways, yet generally on the base of natural bones, as e.g. according to EP-B-141,004. Such a bone replacement material is very useful for certain specific applications, but it has become necessary to replace e.g. vertebral bodies or intervertebral disks as well.

On the base of the prior art, it is the object of the present invention to provide a metal wire structure having various applications, for example as a surface of an endoprosthesis or individually as a bone replacement material; whose pore structure allows a good ingrowth of bone tissue, and which yields a relatively high motional elasticity, whereby a permanent anchorage of the prosthesis is ensured, and which furthermore allows a simple manufacture adapted for all prosthesis parts.

This object is attained by means of a metal wire structure, consisting of a sintered hollow mesh knitting which is formed of elastic metal wires.

The invention is hereinafter described in more detail with reference to a drawing of embodiments.

FIG. 1 schematically shows a single-layer wire knitting according to the invention in a plan view;

Figure 1:
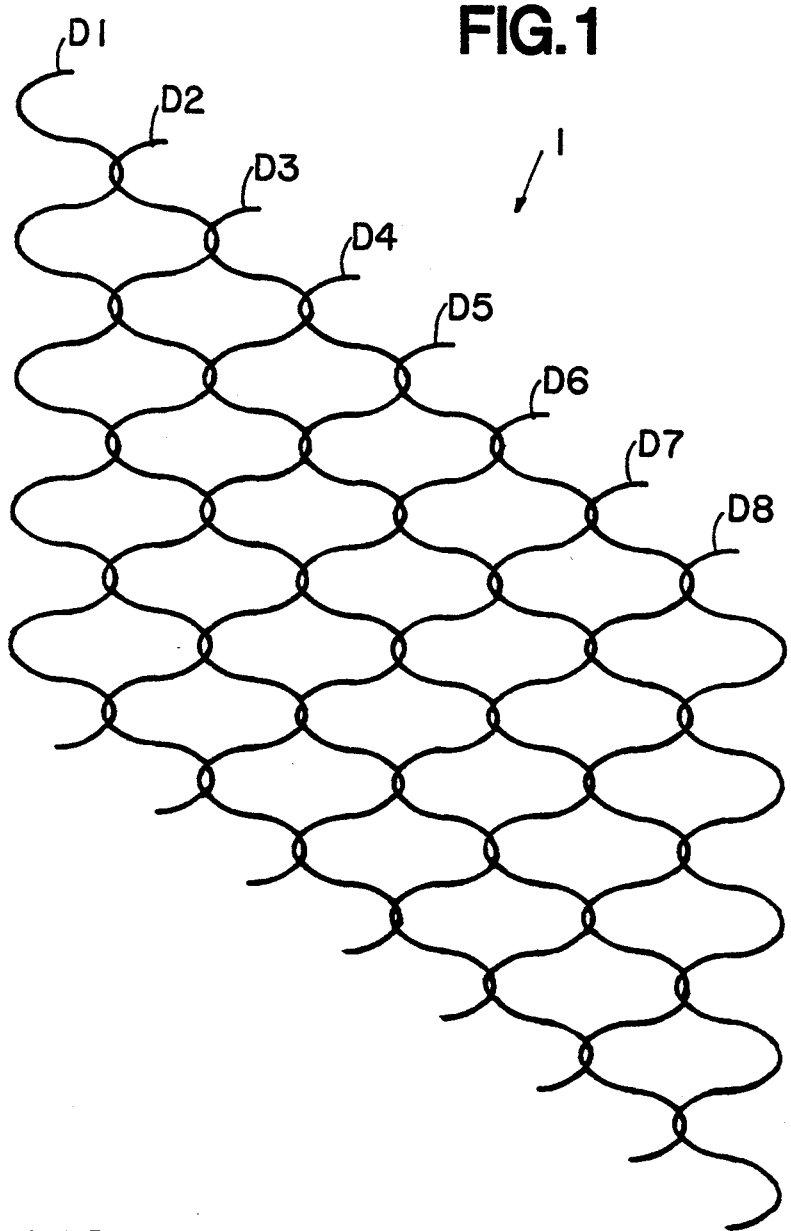
Figure 2:
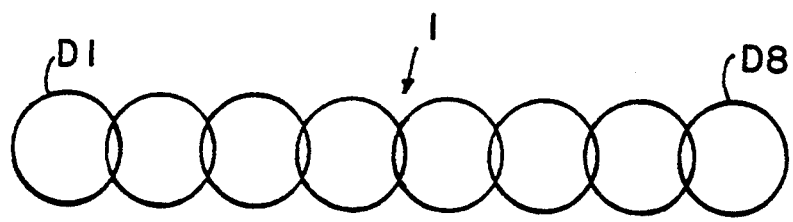
FIG. 2 shows a cross-section of FIG. 1.

Metal wires which are compatible with the body are used as a basic material for the manufacture of the wire knitting according to FIGS. 1 and 2, wires having a high ductility being particularly suitable, such as titanium, stainless steel or other special steel wires; cobalt-chrome, cobalt-molybdene, titanium or gold alloy wires. Such wires are commercially available. As a rule, single wires are used, but braided wires may be used for special applications. The wire thickness is adapted to the size of the implant body or of the implant, respectively, and is comprised between 0.030 and 1.0 mm, preferably in the order of 0.1 to 0.5 mm, while the open pore size is in the order of 0.2 to 1.5 mm according to the intended use, see examples I–II.

The manufacture of the single-layer wire knitting according to FIGS. 1 and 2 is effected with known wire knitting machines as are usual e.g. in the jewellery industry, where such wire knitting machines are used for the manufacture of flexible necklaces or bracelets. In this context, it is preferably intended to realize said knitting in the form of entwined and interconnected spiral springs. In the first place, spiral springs comprise the possibility of designing spiral loops of different diameters and different pitches, and thus allow a variable porosity. Moreover, they comprise in a particular way the desired elastic spring principle which allows an especially good adaptability to differently shaped prosthesis surfaces or as an implant in the unsintered state, but which also ensures a relatively high elastic mobility of the meshes in the sintered state, so that the latter may easily follow the elastic deformations of the bone according to the above-mentioned objectives.

Furthermore, the spiral spring compound is relatively easy to manufacture. The principle of the elastic spring compound is known in the jewellery industry as a so-called "rete milanese". In the textile industry, such hollow mesh knittings are also known as knitted or warp-knitted fabrics. In the jewellery industry, however, this knitting is generally used in a flexible, unsintered form and moreover flattened by pressing. In contrast, the knitting of the invention merely serves as a well-adaptable intermediate product which is only given the desired stability by the following sintering process while conserving a relatively high elasticity, and which would lose the desired pore structure in the pressed state. If a knitted fabric hose, e.g. according to U.S. Pat. No. 4,064,567, were applied to prosthesis shafts without sintering, said knitted fabric would be crushed already when the prosthesis is inserted, and under load would result in a continuous chafing friction with considerable metal abrasion and a consequent inflammation of the tissue due to foreign matter in the sense of the so-called metallosis.

As any other knitted fabric, said metallic hollow mesh knittings may be knitted to form the most diverse parts and shapes, most economically in the form of so-called endless fabric, and are then cut to the desired size and shape for application, e.g. in the form of short hose sections for attachment to prosthesis rods, or in the form of oval parts to be sintered onto disk-shaped prosthesis support surfaces, e.g. for tibia plateaus or knee prostheses.

After the attachment or application to metallic anchorage surfaces of the prostheses, the loosely coated prostheses are conveyed to a sintering furnace which, according to the metal type, is usually under vacuum or comprises an inert gas atmosphere. In said sintering furnace, said metal wire knitting is sintered onto the support surface, and the mesh contact surfaces are sintered together by means of low temperature sintering (diffusion adhesion) at temperatures of 600° to 700° C. Instead of sintering the knitting onto the metal prosthesis, it is also possible to presinter said knitting and subsequently to attach it to the prosthesis by riveting, welding, screwing or clamping.

For the coating of prostheses of a thermoplastic synthetic material such as polyethylene, the flat, hood-shaped or hose-shaped knittings are applied in a heated condition to the coating surfaces of said plastics material which are softened by the heat and pressed in to such an extent that the loops of said knitting are only partly melted into said plastics material while partly protruding therefrom, so as to allow an ingrowth of the bone into the free portions and thus an "ingrowth fixation" of the prosthesis.

Figure 3:
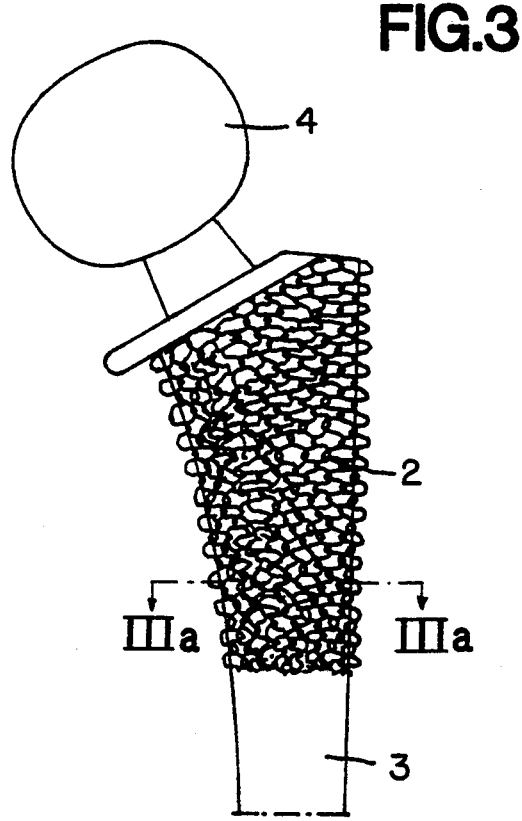
FIG. 3 shows a cross-section of an endoprosthesis which is coated with the knitting of FIG. 1.
Figure 3A:
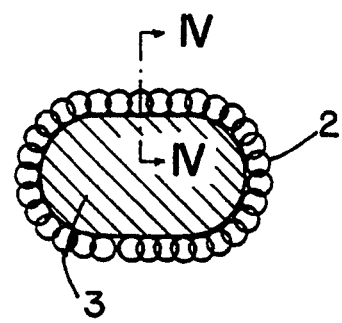
FIG. 3a shows a cross-section according to line IIIa—IIIa of FIG. 3.

FIG. 1 shows a possible embodiment of a knitting where the spiral-shaped wires D1, 3, 5, 7 etc. are visible which are entwined with wires D2, 4, 6, 8 etc., see also FIG. 3a. This knitting corresponds to the above-mentioned "rete milanese" type.

Figure 15:
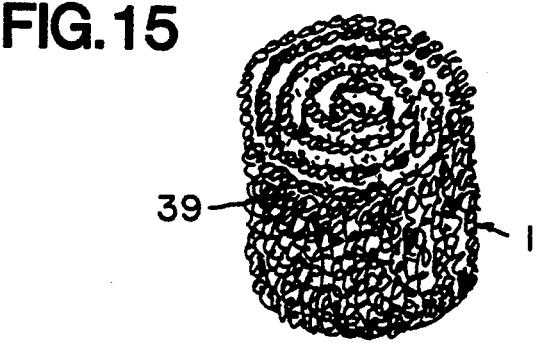
Figure 16:
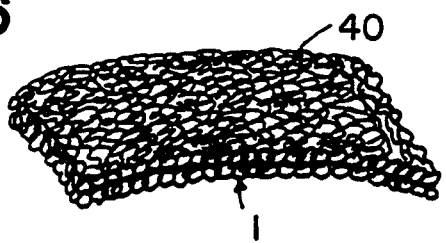
FIG. 16 shows the application of the knitting of the invention as a flat bone replacement.

For special purposes it may be advantageous to use multiple layer knittings, either by stacking the knittings and only sintering them together (see examples of FIGS. 14–16), or by manufacturing multiple layer knittings from the beginning. This would be feasible when using "rete milanese" in particular.

The attachment of cylindrical hoses 2 to conical prosthesis shafts 3 (see FIG. 3) results in that the knitting forms stretched, i.e. extended and larger mesh spaces in the larger portion than in the narrower portion, where the meshes are more compressed and thus form smaller pores. Yet this is no disadvantage since a stronger attachment in the larger pores by means of correspondingly stronger bone projections in the bone area near the joint (epi-methaphysis) and a slightly lesser indentation in the central area of the bone shaft (diaphysis) is intended, which is not only true for hip joint prostheses. Alternatively, it would be possible in this case to manufacture conical knittings having an increasing or conversely decreasing number of meshes from the beginning, as is usual in textile knitting.

Of course, as the case may be, other forms of knittings which are different from the previously described endless knittings or conical knittings may be produced for a better adaptation to the prosthesis shape or the desired bone replacement, e.g. in the form of hoods, pockets, cylindrical rolls etc.

The hollow mesh knitting of the invention may be used for all kinds of prostheses such as shoulder, elbow, finger, hip joint, knee, ankle, and toe joint prostheses, as well as for the replacement of shaft bones and as a bone replacement for vertebrae, etc.

Besides the already mentioned wire materials, it is also possible to use wires with osteotrophicbioactive properties or correspondingly, to coat already sintered knittings subsequently with calcium salts, in particular also with hydroxyl apatite, the plasma spray method being used, for example. The accretion of the bone to the thus bioactivated metal surfaces of the prosthesis rod and mainly also of the knitting coating may thereby be accelerated.

Practical Examples

1. Hip joint prosthesis according to FIG. 3

A knitting I of the "rete milanese" type made of 0.3 mm titanium wire having a mesh diameter of 2 mm and thus a central pore size of 1.2 mm in the form of a hose with a hose diameter of 20 mm is attached to the proximal first third, i.e. over a length of about 60 mm, of a conical hip prosthesis rod 3 made of high-strength titanium alloy and having a length of about 180 mm in such a manner that said knitting is tightly applied and strongly stretched in the upper area and in the unstretched state in the lower area. As the case may be, a circular titanium wire thread may be added for securement, or the hose may be spiraled up in order to increase the tension.

Subsequently, said titanium wire mesh is sintered to said rod and the mesh contact points are sintered together in a sintering furnace, either under vacuum or in an argon atmosphere. After further treatment, such as conical milling for the attachment of a metallic or ceramic hip ball 4 and cleaning, the prosthesis part is prepared for packing, sterilisation and implantation.

Figure 4:
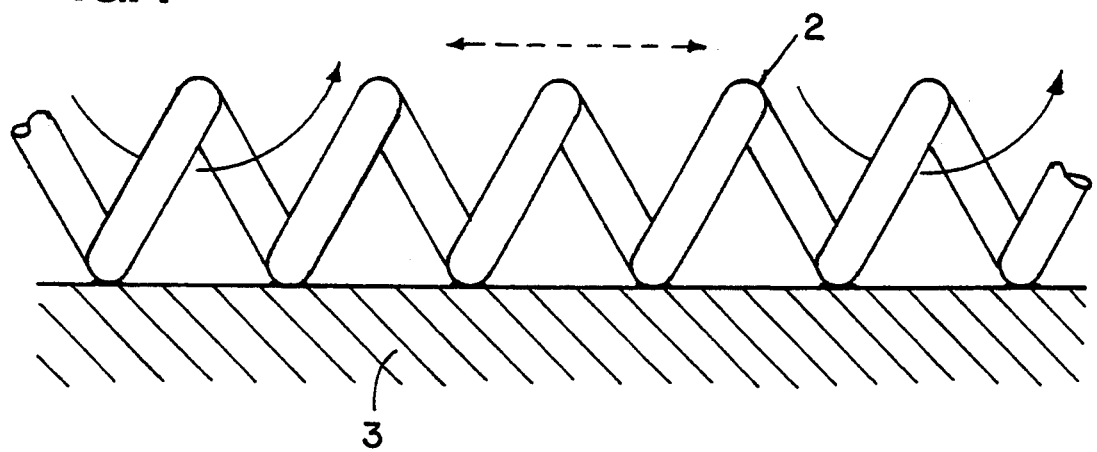
FIG. 4 shows a cross-section according to line IV—IV of FIG. 3a on an enlarged scale.

FIG. 4 schematically shows how the large mesh spaces facilitate the ingrowth of bone tissue K, as symbolized by arrows, and the relatively high elastic mobility (dotted arrow) is conserved even after the sintering process.

Figure 5:
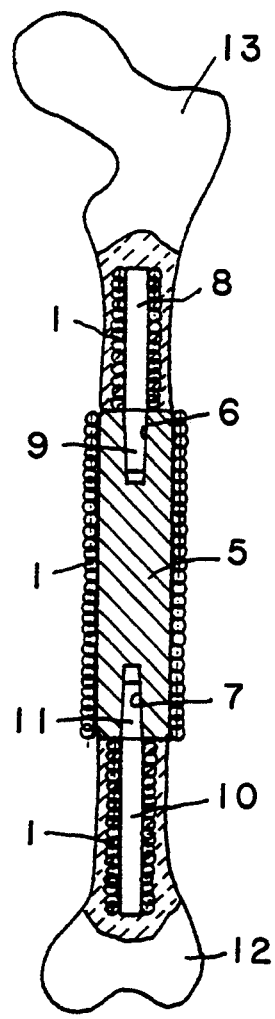
FIG. 5 shows an application of the knitting of FIG. 1 for an intermediate piece of the femur bone shaft.

2. Intermediate piece of the femur bone shaft according to FIG. 5

Cylindrical intermediate piece 5 is provided at both ends with a respective conical bore 6 resp. 7 wherein anchorage rods are inserted. Proximal anchorage rod 8 has a cone 9 corresponding to said conical bore and is manufactured in a variable length, while distal anchorage rod 10 has a corresponding cone 11. The intermediate piece may have an adapted, variable length as well. Both the anchorage rods and intermediate piece 5 are covered with the knitting 1 of the invention and subsequently sintered as in the previous example. Beforehand, the knitting may be fastened by means of single wire loops.

Figure 6:
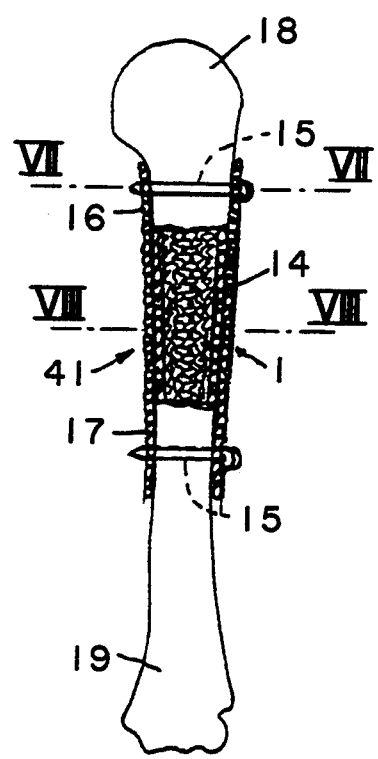
FIG. 6 shows an application of said knitting for an intermediate piece of the humerus bone shaft.
Figure 7:
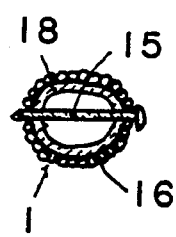
FIG. 7 shows a cross-section according to line VII—VII of FIG. 6.
Figure 8:
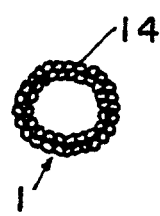
FIG. 8 shows a cross-section according to line VIII—VIII of FIG. 6.

3. Intermediate piece of the humerus bone shaft according to FIG. 6

Intermediate bone shaft 41 is formed of a double-layered knitting 14 which is adapted to be secured by means of screws 15 to a stump 16 resp. 17 of bone sections 18 resp. 19 and is subsequently sintered as in the previous examples.

Figure 9:
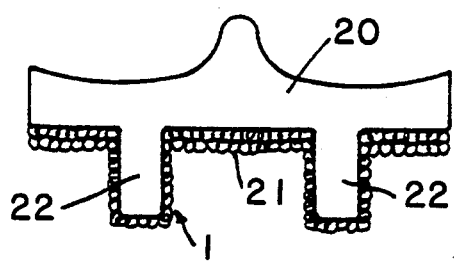
FIG. 9 shows an application of the knitting of the invention for a plastics tibia head prosthesis.

4. Tibia head prosthesis according to FIG. 9

Tibia head prosthesis 20, which is known per se, is provided on its underside with a double-layered knitting 21, while anchorage peg 22 is coated with single layer knitting 1, whereupon said coatings are partially pressed in under heating.

Figure 10:
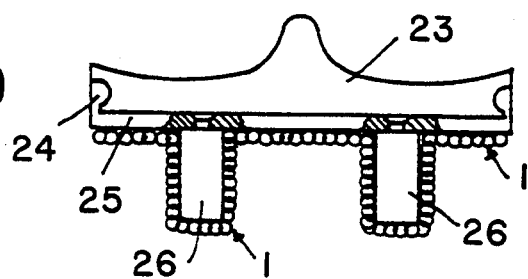
FIG. 10 shows an application of the knitting of the invention for a plastics tibia head prosthesis on a metal washer.

5. Tibia head prosthesis on metal washer according to FIG. 10

Plastics tibia head prosthesis 23 is connected by a snap lock 24 with a metal washer 25. Anchorage pegs 26 are screwed into said metal washer 25. Here also, both the underside of the prosthesis and said pegs are provided with a knitting 1, said knitting being sintered on in a sintering furnace as previously described. In this case it is useful to press said wire knitting against the lower plateau side by means of detachable clamps. After the sintering process, the pressing clamps are removed, the prosthesis piece is cleaned and subjected to further machining and then radiation sterilized and packaged.

Figure 11:
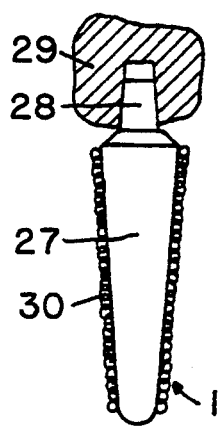
FIG. 11 shows an application of the knitting of the invention for a tooth root in a sectional view.

6. Tooth root prosthesis according to FIG. 11

Tooth root prosthesis 27, having e.g. a length of 20 mm and being conically tapered with an upper diameter of 4 mm, is provided with a plug-in cone 28 for receiving a build-up such as a crown 29 or a denture, fitted with a fine, hose-shaped wire knitting 30 having a wire diameter of 0.1 mm and a pore size of 0.25 mm, and conveyed to a sintering furnace wherein said knitting is sintered together with said anchor. This is followed by the usual cleaning, fine-machining, sterilisation and packaging.

Figure 12:
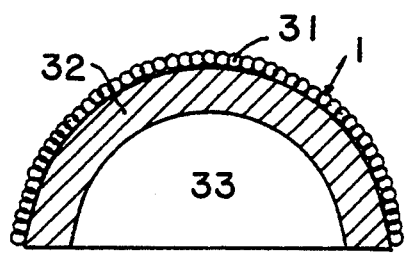
FIG. 12 shows an application of the knitting of the invention for a hip joint socket prosthesis in a sectional view.

7. Hip joint socket according to FIG. 12

First, a hemispherical, cap-shaped wire knitting 31 having a diameter of e.g. 50 mm is produced and fitted to a ceramics ball of the same diameter and subjected to a contact sintering of the mesh contact points. An internally reinforced, yet elastic wire mesh hemisphere is thus obtained, which is now placed upon a hemispherical hip joint socket 32 of plastics material having the same external diameter of 50 mm and is pressed upon the latter under heating to the flowing temperature of the plastics material, so that the metallic loops of the knitting partially penetrate into the softened plastics surface and are solidly indented therein. After cooling, said plastics material is securely connected to the hemispherical metallic sintered wire knitting. Thereafter, by means of a finishing process involving a cutting process or a thermal surface-finishing pressing, the actual socket cavity 33 is created for the reception of a hip joint ball having a usual hip joint ball diameter of e.g. 28 or 321 mm. Radiation sterilisation and packaging are effected subsequently.

Of course, a hip joint socket having another external shape, e.g. a conical shape, may be concerned, with a corresponding presintered knitting. In this case, as in the previous examples, polyethylene is generally used as a plastics material, but another suitable material may naturally be used as well.

Figure 13:
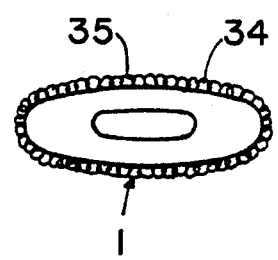
FIG. 13 shows an application of the knitting of the invention for an artificial intervertebral disk.

8. Artificial intervertebral disk according to FIG. 13

A disk-shaped plastics piece 34 having a diameter of e.g. 30 mm is first produced by means of a cutting or a pressing process. After sintering and hardening, identically sized sections of an endless titanium wire knitting 35 are applied to the surface of the upper and the lower sides of the polyethylene piece and conveyed to a warming furnace whose temperature is increased up to the melting limit of the plastics material. As the upper and the lower side of the plastics material begin to melt, the two wire mesh disks are mechanically or hydraulically pressed into the polyethylene surface in such a manner that the plastics material flows around the adjoining portions of the knitting meshes and the knitting is thus attached to the plastics material after cooling while remaining partially exposed for the ingrowth of the bone.

Alternatively, in order to obtain an improved elastic damping, a slightly spherical, vaulted plastics disk may be produced and centrally excavated, which will finally be provided on its slightly vaulted surfaces with a correspondingly shaped, presintered wire knitting in the same manner.

However, it is also possible to introduce the plastics core into a pocket-shaped knitting of a fitting size and afterwards to produce the thermal pressing connection between said wire knitting and said plastics material. Polyethylene is advantageously used for the production of artificial intervertebral disks.

9. Vertebral body replacement according to FIG. 14

Figure 14:
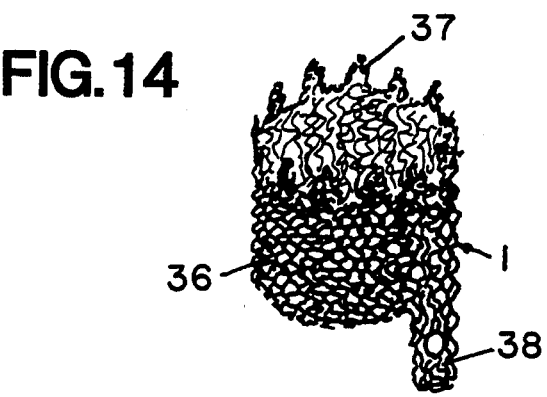
FIGS. 14 and 15 show the application of the knitting of the invention as a vertebral body replacement.

As mentioned in the introduction, it is also possible to use the knitting of the invention individually, i.e. as opposed to a coating on a prosthesis. Vertebral body replacement 36 according to FIG. 14 is formed of a double-layered hollow knitting cylinder which has been produced and sintered according to the invention. For its connection to the non-represented bone parts, said vertebral body may either have a crown-shaped toothed anchorage 37 or a connection by means of a screwable tab 38 according to FIG. 14.

10. Vertebral body replacement according to FIG. 15

This vertebral body 39 is formed of a rolled and sintered knitting, the anchorage being effected as represented or by means of toothed anchorage 37 or screwable tab 38 in analogy to FIG. 14.

11. Flat bone replacement according to FIG. 16

The multiple-layered and sintered knitting 40 may be used in a predetermined size as a replacement for flat bones such as skull bones or pelvis bones.

It is clearly apparent in the description that the shown examples are only a selection of the possible applications while a number of further applications in the field of endoprosthetics are possible. The same applies both for the material used in the manufacture of the knitting and for the materials serving as a support, i.e. as a prosthesis.

We claim:

1. A metal wire structure for prosthetics, consisting of a sintered, hollow mesh knitting covering an external surface of a prosthesis, said knitting being formed of elastic metal wires and consisting of a plurality of interconnected spiral springs, each entwined and sintered together to form an elastic layer, said knitting defining a rete milanese structure.

2. The metal wire structure of claim 1, wherein said elastic layer is sintered onto a metal prosthesis.

3. The metal wire structure of claim 1, wherein said elastic layer is partially melted into a surface of a plastic prosthesis.

4. The metal wire structure of claim 1, wherein said elastic, metal wires are made of titanium, stainless steel, a cobalt-chrome, a cobalt molybdene, a titanium, or a gold alloy.

5. The metal wire structure of claim 1, wherein said spiral springs form a porous structure consisting of pores each having a diameter in the range of 0.2 to 1.5 mm, said wires having a diameter in the range of 0.03 to 1.0 mm.

6. The metal wire structure of claim 1, wherein said metal wire structure has osteotrophic-biactive properties.

7. The metal wire structure of claim 1, wherein said spiral springs form a porous structure consisting of pores having different sizes.

8. The metal wire structure of claim 1, wherein said metal wire structure is coated with calcium salts.

9. The metal wire structure of claim 1, wherein said metal wire structure is coated with a material substantially comprising hydroxyl apatite.

10. The metal wire structure of claim 1, wherein said metal wire structure is coated with a ceramic material.

11. A prosthetic device consisting of:
a prosthesis; and
a metal wire structure covering an external surface of said prosthesis, said metal wire structure comprising a sintered, hollow mesh knitting which is formed of elastic metal wires, said knitting consisting of a plurality of interconnected spiral springs, each entwined and sintered together to form an elastic layer, said knitting defining a rete milanese structure.

12. The prosthetic device of claim 11, wherein said prosthesis comprises a metal structure, and said elastic layer is sintered onto said metal prosthesis.

13. The prosthetic device of claim 11, wherein said prosthesis comprises a plastic structure, and said elastic layer is partially melted into a surface of said plastic prosthesis.

14. The prosthetic device of claim 11, wherein said metal wire structure has osteotrophic-biactive properties.

15. The prosthetic device of claim 11, wherein said spiral springs form a porous structure consisting of pores having different size.

16. The prosthetic device of claim 11, wherein said metal wire structure is coated with calcium salts.

17. The prosthetic device of claim 11, wherein said metal wire structure is coated with a material substantially comprising hydroxyl apatite.

18. The prosthetic device of claim 11, wherein said metal wire structure is coated with a ceramic material.

* * * * *